United States Patent [19]

Robbins et al.

[11] Patent Number: 4,788,296

[45] Date of Patent: Nov. 29, 1988

[54] PROCESS FOR THE PRODUCTION AND RECOVERY OF TRIMELLITIC ANHYDRIDE

[75] Inventors: Bonnie M. Robbins, St. Charles; Joseph P. Egan, Downers Grove; Daniel A. Morlang, Joliet; Aaron R. Slagel, Morris, all of Ill.

[73] Assignee: Amoco Corporation, Chicago, Ill.

[21] Appl. No.: 56,118

[22] Filed: May 29, 1987

[51] Int. Cl.$^4$ .......... C07D 307/89

[52] U.S. Cl. .......... 549/245

[58] Field of Search .......... 549/245

[56] References Cited

U.S. PATENT DOCUMENTS 3,484,458 12/1969 Stein et al. .......... 549/245

4,587,350 5/1986 Kilner et al. .......... 549/245

*Primary Examiner*—Richard L. Raymond

*Attorney, Agent, or Firm*—Frederick S. Jerome; William H. Magidson; Ralph C. Medhurst

[57] ABSTRACT

An integrated process for manufacture of trimellitic acid anhydride by the steps of catalytic oxidation of pseudocumene in the presence of acetic acid in an oxidation zone wherein liquid-phase conditions are mantained, cooling the oxidation reaction effluent to crystallize trimellitic acid, separating and recovering crystallized trimellitic acid, conducting the thermal conversion of the trimellitic acid to its anhydride continuously in two series staged dehydration zones and evaporating acetic acid solvent and hydrocarbon. Vapor from the first dehydration zone and the acetic acid mother liquor are combined as feed for distilling acetic acid and water mixture therefrom leaving a residue having high melting solids. The residue is combined with a bottom fraction from distillation of trimellitic anhydride product having catalyst metals and the combined material is added to the first dehydration zone in an amount of up to about 50 weight percent of the combined residue and bottom fraction.

5 Claims, 3 Drawing Sheets

PROCESS FOR THE PRODUCTION AND RECOVERY OF TRIMELLITIC ANHYDRIDE

BACKGROUND OF THE INVENTION

This invention relates to a process for manufacture of trimellitic acid anhydride from 1,2,4-trimethyl benzene, commonly known as pseudocumene, and more particularly relates to a method of recovering pure trimellitic anhydride from the reaction mass obtained by the liquidphase oxidation of pseudocumene by air or oxygen.

The process of this invention provides a commercial process for the manufacture of 4-carboxyphthalic anhydride through the catalytic liquid phase oxidation of commercially available 1,2,4-trimethylbenzene (pseudocumene) with air in the presence of acetic acid as reaction solvent, separation and recovery of crystalline trimellitic acid from the oxidation reaction effluent, thermal dehydration of trimellitic acid to its anhydride and separation and recovery of that anhydride from intermediate oxidation by-product and other oxidation by-product impurities by distillation and/or vaporization process steps.

Pseudocumene is oxidized with air mainly to a mixture of dimethylbenzoic acids in the presence of catalysis provided only by cobalt and/or manganese oxidation catalysts under liquid phase conditions using acetic acid as the reaction solvent. By the use of oxygen as oxidant and a combination of cobalt as metal oxidation catalyst and alpha-methylenic ketones as side chain oxidation initiator or promoter, pseudocumene is oxidized mainly to a mixture of 2-methylterphthalic acid and 4-methyl isophthalic acid in the presence of acetic acid solvent and under liquid phase conditions at atmospheric pressure. Catalytic liquid phase oxidation of pseudocumene with air can be accomplished in the presence of acetic acid solvent and the catalysis provided by the combination of heavy metal oxidation catalyst and a source of bromine as disclosed and claimed in U.S. Pat. No. 2,833,816. This oxidation method using a combination of heavy metal oxidation catalyst and a source of bromine to provide catalysis describes the production of 92 weight percent trimellitic acid filter cake product in a two hour reaction at 198° C. (about 390° F.) The theoretical yield of trimellitic acid from pseudocumene is 175 weight percent. However, the oxidation method of U.S. Pat. No. 2,833,816 has been developed to produce total trimellitic acid yields in the range of 135 to 161 weight percent or about 77% to about 92% of theory based on the pseudocumene hydrocarbon feed. By total yield of trimellitic acid is meant all of the trimellitic acid in the oxidation reaction effluent.

The more highly developed catalytic liquid phase air oxidation of pseudocumene by the method of U.S. Pat. No. 2,833,816 using the catalysis provided by the combination of heavy metal oxidation catalysts therein defined with bromine or a source of bromine under liquid phase oxidation conditions produces total trimellitic acid yields of 135 to 161 weight percent based on commercially available pseudocumene. But, even then, there are also coproduced trimesic acid, iso- and terephthalic acids, 4-methylorthophthalic acid, 2-methylterephthalic acid, 4-methylisophthalic acid and formyl phthalic acids in amounts as to present substantial problems in the recovery of high quality trimellitic acid, dehydration of trimellitic acid to its intramolecular anhydride and recovery of that anhydride.

Another problem in the manufacture of trimellitic acid through the oxidation of pseudocumene to trimellitic acid in the presence of acetic acid comes from the relatively high solubility of trimellitic acid in acetic acid. This solubility goes from about 1.0 pound per 100 pounds glacial acetic acid at 80° F. to 6.5 pounds per 100 pounds glacial acetic acid at 220° F. The presence of water in the acetic acid increases the solubility of trimellitic acid so that in aqueous acetic acid solvent having 82 to 85% acetic acid and 18 to 15% water by weight there are dissolved at 80° and 220° F. about 3.2 pounds and 16.5 pounds trimellitic acid per 100 pounds solvent. Ordinarily aqueous acetic acid of 90 to 98% (10 to 2% water) by weight is used in the oxidation as solvent not only because acetic acid of higher strength is more expensive to recover but also because the presence of 2 to 10% water by weight substantially eliminates oxidation induction. During oxidation of the methyl groups to carboxylic acid groups water is produced as a by-product and is generally retained through the removal of heat of reaction by condensing the acetic acid and water boil up from the liquid phase in the oxidation zone and returning to condensate to the oxidation zone. The aqueous acetic acid solvent in the effluent removed from the oxidation zone can contain about 10 to 25% water (90 to 75% acetic acid) by weight when the 90 to 98% aqueous acetic acid solvent is used in the weight ratios of 5 to 2 parts per part of pseudocumene. Thus at usual crystallization temperatures of 60° to 120° F. a substantial amount of trimellitic acid remains in solution.

For example, in Example II of U.S. Pat. No. 3,161,658 there is described the cooling to 100° F. of an oxidation reaction effluent containing for each 500 parts acetic acid solvent 200 parts trimellitic acid and 50 parts of pseudocumene oxidation intermediates. There was recovered 135 parts crystalline trimellitic acid per 500 parts of acetic acid solvent. Thus, of the originally produced 200 parts trimellitic acid there was left in solution 65 parts or 32.5%. This appears to have been an oxidation of pseudocumene conducted in the presence of acetic acid solvent in the ratio of about 3.5 parts solvent per part of pseudocumene. Higher ratios of solvent to pseudocumene would have caused a greater proportion of the total trimellitic acid to remain in solution at 100° F. For example, at a 5 to 1 solvent ratio 45% of the trimellitic acid produced would have remained in solution at crystallization and filtration temperatures of 100° F.

U.S. Pat. No. 3,161,658 provides one technique for recovering the trimellitic acid remaining dissolved in the aqueous acetic acid mother liquor. This is done by adding the mother liquor to a pool of molten trimellitic anhydride (370°-375° F.) and flashing off water and acetic acid vapors and drawing off from the molten pool liquid in an amount equivalent to the weight of solids charged with the mother liquor. This liquid draw off is solidified, ground and dissolved in a dialkyl ketone or aromatic hydrocarbon (the ketone solution must be filtered to remove insolubles) and the solution is combined with anhydride from dehydrated 100° F. filter cake. The aromatic hydrocarbon solution is filtered to remove an insoluble oily residue and the filtrate cooled to 75° F. to precipitate trimellitic anhydride. This anhydride can be added to the anhydride from dehydration of 100° F. first filter cake. By simple flashing at 6 mm Hg absolute there is recovered a trimellitic anhydride product of 95% anhydride content, 95% pure in yields of 85 to 90% based on the trimellitic acid produced by the oxidation. However, the ketone and aromatic hydrocarbon solvents are flammable and their foregoing uses although advantageous do present fire hazards.

Other problems in the recovery of trimellitic anhydride from trimellitic acid produced by catalytic liquid phase air oxidation in acetic acid solvent arises in the distillative and/or evaporative separation of trimellitic anhydride from the melt produced by dehydrating trimellitic acid. In this melt there is a substantial amount of iso- and terephthalic acids produced mainly as coproducts of oxidation and some by decarboxylation of trimellitic acid when the dehydration is carried out at temperatures of 410° to 428° F. or higher. The literature reports that trimellitic acid is dehydrated to its anhydride at 216° C. (about 421° F.). But at 410° to 428° F. some decarboxylation takes place not to produce phthalic anhydride only but rather to produce mainly iso- and terephthalic acids. However, this decarboxylation can be substantially eliminated during dehydration by operating at about 335° to 400° F. with an inert gas sweep. This is disclosed and claimed in U.S. Pat. No. 2,971,011. The gas sweep is conducted with gas inert to trimellitic anhydride at 335° to 400° F. Nitrogen, flue gas, $CO_2$, hydrocarbon vapors and even steam can be used as inert gas.

Such gas sweep dehydration does not eliminate the problem caused by the presence of oxidation by-products iso- and terephthalic acids. When either or both of isophthalic acid and terephthalic acid are present in the molten trimellitic anhydride to be recovered by distillative and/or evaporative techniques they are carried over with the trimellitic anhydride vapors after the amounts thereof in the molten anhydride bottoms reaches their saturation concentrations. This, of course, adversely affects the clarity and purity of recovered molten trimellitic intramolecular anhydride and the reactivity of the anhydride.

The intramolecular anhydride of trimellitic acid has become a commercial starting material for surface coatings having the desired properties of high thermal decomposition, high temperature insulating properties and good resistance to chemical attack and are substantially insoluble. These surface coatings are obtained from prepolymers prepared, for example, from trimellitic intremolecular anhydrides and polyamines. Because of the trifunctionality of the intramolecular anhydride the final surface coating product is a polyimide-amide. The intramolecular anhydride of trimellitic acid also has become a starting material for solid foams obtained by reacting an isothiocyanate among other reactants with the intramolecular anhydride. Air and heat drying points and enamels with hydrocarbon or water solvent vehicles are also prepared from the intramolecular anhydride of trimellitic acid. For most of these uses, trimellitic acid intramolecular anhydride of an anhydride purity of 98 to 99% is required.

For many commercial applications mentioned above color of the trimellitic anhydride has become an important specification. Highly colored brown, tan, or even yellow products may no longer be acceptable. Triethylene Glycol (TEG) color is a typical standard measure of this performance quality of trimellitic anhydride. In this method a reaction of the trimellitic anhydride with a 300% molar excess of triethylene glycol is carried out at 500° F. (about 260° C.) to produce a solution whose color is matched instrumentally with APHA color standards. Reaction time is sixty minutes. A typical commercial product must have a TEG color of 170 or less.

The problems that require solving are the recovery of trimellitic acid anhydride in yields above 85 to 90% based on trimellitic acid produced by catalytic liquid phase oxidation of pseudocumene with air in the presence of acetic acid solvent, the increase of recovery of trimellitic acid from the oxidation reaction effluent, an improved distillative and/or evaporative process for separating the intramolecular anhydride from the crude anhydride melt obtained by the dehydration of impure trimellitic acid, elimination of the fire hazards accompanying the use of dialkyl ketones or aromatic hydrocarbon extract solvents previously disclosed for advantageous use in increasing the recovery of trimellitic acid anhydride and the other problems before mentioned.

U.S. Pat. No. 4,587,350, incorporated by reference herein, discloses a process for the oxidation of pseudocumene to trimellitic acid by a catalytic oxidation of pseudocumene with air in the presence of acetic acid in a oxidation zone in the liquid phase with catalysts comprising zirconium, cobalt, and manganese and a source of bromine.

The process of this invention provides an integrated system for the commercial production of trimellitic acid anhydride.

SUMMARY OF THE INVENTION

A process for the manufacture of trimellitic acid anhydride by the steps of catalytic oxidation of pseudocumene in the presence of acetic acid in an oxidation zone wherein liquid-phase conditions are maintained and the catalyst comprises one or more heavy metal oxidation catalysts comprising zirconium, cobalt, and manganese and a source of bromine, cooling the oxidation reaction effluent to crystallize trimellitic acid, separating and recovering crystallized trimellitic acid from the acetic acid solvent mother liquor, distilling from the acetic acid mother liquor to obtain a mixture of acetic acid and water for concentration of the acetic acid content to provide acetic acid solvent concentrate for recycle to the oxidation and to obtain a bottoms fraction having high melting solids, heating the crystalline trimellitic acid to convert it to its anhydride and distilling the anhydride to obtain trimellitic acid anhydride product. The improvement arises from conducting the thermal conversion of the trimellitic acid to its anhydride continuously in two series staged dehydration zones with heat removal by evaporation from the liquid in each of the dehydration zones, thereby converting trimellitic acid to its anhydride and evaporating acetic acid solvent and hydrocarbon. The crude trimellitic anhydride is purified by distillation and condensing the vaporized overhead fraction to obtain trimellitic anhydride product. In the present novel integrated process for commercial production of trimellitic anhydride the vapor from the first dehydration zone and the acetic acid mother liquor are combined as feed for distilling acetic acid and water mixture therefrom leaving a residue having high melting solids. The residue is combined with the bottom fraction from the distillation of the trimellitic anhydride having catalyst metals and the combined material added to the first dehydration zone in an amount of up to about 50 weight percent of the combined residue and bottom fraction.

BRIEF DESCRIPTION OF THE INVENTION

We have discovered an improved process for the manufacture of trimellitic acid anhydride by the steps of catalytic oxidation of pseudocumene in the presence of acetic acid in an oxidation zone wherein liquid-phase conditions are maintained and wherein the weight ratio of acetic acid to pseudocumene is in the range of about 0.5:1.0 to about 5.0:1.0 and the catalyst comprises one or more heavy metal oxidation catalysts comprising zirconium, cobalt, and manganese to provide about 0.1 to about 0.4, preferably about 0.22 to about 0.32, weight percent total metals based on pseudocumene and a source of bromine and to provide a total of about 0.10 to about 0.30 weight percent total bromine based on pseudocumene, wherein the total weight ratio of bromine ions to total metal ions is about 0.5 to about 2.0, the zirconium content is about 1 to about 5%, preferably about 2.0 to about 4.0, and the manganese content is about 14 to about 60%, each metal by weight of the total metals and wherein the cobalt content is about 35 to about 80 weight percent, temperatures in the oxidation are in a range of about 220° F. to about 480° F., preferably about 300° F. to about 430° F., cooling the oxidation reaction effluent to crystallize trimellitic acid, separating and recovering crystallized trimellitic acid from the acetic acid solvent mother liquor, distilling from the acetic acid mother liquor to obtain a mixture of acetic acid and water for concentration of the acetic acid content to provide acetic acid solvent concentrate for recycle to the oxidation and to obtain a bottoms fraction having high melting solids, heating the crystalline trimellitic acid to convert it to its anhydride and distilling the anhydride to obtain trimellitic acid anhydride product. The improvement arises from conducting the thermal conversion of the trimellitic acid to its anhydride continuously in two series staged dehydration zones with heat removal by evaporation from the liquid in each of the dehydration zones. The first dehydration zone is operated at a temperature in the range of about 400° to about 500° F., preferably about 420° to about 480° F., and at a pressure in the range of about 10 to about 25 pounds per square inch absolute and the second dehydration zone is operated at a temperature in the range of about 400° to about 500° F., preferably about 420° to about 490° F., and a pressure in the range of about 50 to about 400 mm. Hg thereby converting trimellitic acid to its anhydride and evaporating acetic acid solvent and hydrocarbon. The crude trimellitic anhydride is purified by distillation at a temperature in the range of about 425° to about 575° F., preferably about 450° to about 550° F., and an absolute pressure of about 4 to about 400 mm. Hg, preferably about 4 to about 300 mm. Hg, and condensing the vaporized overhead fraction to obtain trimellitic anhydride product. In the present novel integrated proces for commercial production of trimellitic anhydride the vapor from the first dehydration zone and the acetic acid mother liquor are combined as feed for distilling acetic acid and water mixture therefrom leaving a residue having high melting solids. The residue is combined with the bottom fraction from the distillation of the trimellitic anhydride having catalyst metals and the combined material added to the first dehydration zone in an amount of up to about 50 weight percent, preferably about 10 to 45 weight percent, of the combined residue and bottom fraction.

Commercially available pseudocumene is not pure and contains 1 to 5 weight percent of alkyl substituted benzenes having boiling points close to that of pseudocumene such as ethyl toluenes and mesitylene $C_9$ aromatics and even some $C_8$ aromatics such as the xylenes. The ethyl toluenes and xylenes impurities are oxidized to phthalic acids and mesitylene is oxidized to trimesic acid (1,3,5-benzene tricarboxylic acid) at the same time pseudocumene is oxidized to trimellitic acid. It is difficult to convert all of the three methyl groups of pseudocumene to carboxylic acid groups. This difficulty arises from the effect that conversion of one of the two ortho-oriented methyl groups to a carboxylic acid group has on the remaining methyl group. That oxidation difficulty results in the co-production of small amounts of 4-methylorthophahlic acid, 2-methylterephthalic acid and 4-methylisophthalic acid. That oxidation difficulty is in addition to the coproduction of such next to last step oxidation by-products as the formylphthalic acids. The last oxidation step product of pseudocumene is, of course, trimellitic acid.

We have discovered an improved process for the manufacture of trimellitic acid anhydride starting with pseudocumene. The improvement arises from the discovery of a process for recovering trimellitic acid anhydride of 97–98% anhydride content in yields in the range 89 to 90% and higher based on the total trimellitic acid produced by catalytic liquid phase air oxidation of pseudocumene in the presence of catalysis provided by the combination of heavy metal oxidation catalyst and bromine or a source of bromine and in the presence of acetic acid solvent having 93 to 98% acetic acid and 7 to 2% water by weight. The recovery portion of the process of this invention starts with the effluent from the oxidation process which produces 135 to 161 weight percent or more trimellitic acid based on pseudocumene oxidized with air in the presence of 2 to 5 parts of said 93 to 98% aqueous acetic acid solvent as oxidation reaction effluent. Such oxidation reaction effluents contain 182 to 338 parts aqueous acetic acid of about 10 to about 25% water (90 to 75% acetic acid) per 100 parts trimellitic acid, all by weight. Since the anhydride recovery technique of this invention is equally applicable, as will be later apparent, to oxidation reaction effluents having aqueous acetic acid solvent of such wide water variations as 10 to 25 weight percent, there is eliminated the need for having precise control over the water content of the solvent initially charged to the oxidation reaction as before thought or appeared to be needed to aid in the separation and recovery of trimellitic acid.

The suspensions of crystals formed in the crystallization zone is transferred out as feed for a means for separating solids and liquids. Such solid-liquid separation means as continuous centrifuging, filtering, settling, and the like can be used.

The mother liquor from the separation and recovery of crystalline trimellitic acid and vapor from the first acid product dehydration zone are combined as feed for a stripping zone operated at 0 to 10 psig and a feed temperature of 220° F. to 250° F. An external reboiler heats to liquid in the column to 260° F. In this manner water and acetic acid are substantially completely removed as the main feed to the acetic acid concentration and the trimellitic acid in the stripping zone feed contained in the bottoms is converted to the intramolecular anhydride of trimellitic acid in the stripper stillpot. A convenient way to strip out acetic acid and water and at the same time dehydrate trimellitic acid is to use the combined acetic acid mother liquor and condensed dehydration vent vapors as feed to a distillation column whose bottoms liquid is transferred to a stillpot whose temperature is above the melting point of trimellitic anhydride, about 450° F. The bottoms from such a stripping operation are liquid.

The bottoms liquid from the stripping step contains about 5.7% of the total trimellitic acid produced by the oxidation. In the present novel process this anhydride of trimellitic acid is recovered by recycling up to about 50 weight percent, preferably about 25 weight percent, of the liquid from the stripper stillpot to the first acid product dehydrator.

The previously mentioned starting oxidation reaction effluent is obtained by the air oxidation of pseudocumene in the presence of aqueous acetic acid solvent of less than 10 weight percent, preferably 2 to 7 weight percent, water content and in the presence of catalysis provided by the combined use of heavy metal oxidation catalyst and bromine at an oxidation temperature within the range of 320° and 410° F. and a pressure to maintain at least a liquid phase of acetic acid solvent and pseudocumene in the oxidation zone at the operating temperature. Pressures in the range of 140 to 370 psig (pounds per square inch gage) are satisfactory for maintaining necessary liquid phase conditions in the oxidation zone at said operating temperature. The oxidation can be conducted in a batchwise, semi-continuous or continuous manner. By "semi-continuous" is meant charging solvent and catalyst to an oxidation reactor and heating them to reaction temperature and pressure and then simultaneously introducing pseudocumene and air into the oxidation zone with or without additional components of the catalyst system until all the hydrocarbon has been added (i.e. the continuous portion) and then introducing air with or without catalyst components but not hydrocarbon into the oxidation zone (batchwise portion) until the oxidation of pseudocumene is substantially complete, i.e. oxygen is no longer being consumed. Semi-continuous, then in part combines some features of both continuous and batchwise oxidation. Continuous operation can be conducted in one oxidation zone or in a plurality of series connected oxidation zones, preferably four to six, or in a plug flow manner in a pipeline oxidation reactor having one or more than one inlet for catalyst component and/or air injection.

The precise conditions of operation developed for the oxidation of pseudocumene to go from 92 weight percent to 135 to 161 weight percent and higher total trimellitic acid are not material to the understanding and practice of the present invention. Also those precise operating conditions are not a part of this invention. This invention however does depend and uses to advantage the factual existence of the ability to obtain such high conversions of pseudocumene with air as the oxidant, the use of the system of catalyst provided by the combination of heavy metal oxidation catalyst and bromine as taught in U.S. Pat. No. 2,833,816, the use of acetic acid solvent having 95 to 98% acetic acid and 5 to 2% water by weight and the conditions of temperature and pressure before mentioned for liquid phase operation. This high conversion oxidation, then is the starting process step in the combination of process steps that make the total process for obtaining high purity intramolecular anhydride of trimellitic acid in high yields based on the total trimellitic acid produced.

For the understanding and practice of the present invention it is necessary to know the amounts of aromatic co-products and by-products also present in the oxidation reaction effluent. These aromatic co-products and by-products have already been specifically identified by types. Most useful for the understanding and practice of this invention is not the precise amount of each specific aromatic co-product and by-product, but rather, the weight ratio of the total of said aromatic by-products and coproducts related to the trimellitic acid present in the oxidation reaction effluent. The total weight of said aromatic co-products and by-products can be in the ratio range of from 5 to 25 parts per 100 parts of trimellitic acid by weight.

DESIRABLE OPERATING CONDITIONS

Desirable operating conditions for the process steps of this invention are given in the following description. Oxidation reaction effluent is obtained by the oxidation of pseudocumene with air in an oxidation zone at 320° to 410° F. and 140 to 370 psig in the presence of 2 to 3.5 parts inclusive of 94 to 98% aqueous acetic acid (6 to 2% water) per part of pseudocumene of 97 to 99% by weight purity in the presence of heavy metals (e.g. supplied as zirconium acetate, and cobalt and manganese acetate tetrahydrates) in a total concentration of 0.06 to 0.30 weight percent as metals and bromide as provided by hydrogen bromide, sodium bromide, and/or tetrabromoethane in a bromide concentration of 0.1 to 0.7 weight percent. The weight percent of catalyst components are based on the acetic acid solvent. The resulting oxidation effluent withdrawn from the oxidation zone is at 400° to 410° F. and contains trimellitic acid in an amount equivalent to 1.35 to 1.61 pounds per pound of pseudocumene and aromatic impurities in the range of 30 to 5 pounds per 100 pounds of trimellitic acid.

A slurry of trimellitic acid crystals of from 40 to 60% crystal solids by weight is obtained depending upon the portion of water and acetic acid vaporized and removed from a crystallization zone.

The slurry from the crystallization zone is continuously transferred to a rotary vacuum filter, centrifugal filter, or filter press and trimellitic acid crystal cake is separated at 110° to 130° F. The mother liquor is collected in a surge drum. The filter cake contains 15 to 35% acetic acid.

The acetic acid wet filter cake and recycle residue from the mother liquor stripper stillpot are continuously charged by screw conveyor to a boiler containing molten crude trimellitic anhydride at about 450° F. and pressures in a range of about 10 to 25 psia. The hold time in the boiler is about 1 to 2 hours which is sufficient time to assure removal of acetic acid and dehydrate about 85% of the feed trimellitic acid to its anhydride. Some of the anhydride tends to leave the top of the boiler with the acetic acid vapors. These vapors are transferred to the stripper feed vessel and combined with the mother liquor.

Liquid is withdrawn continuously from the first dehydration zone and fed into the second dehydration zone operated at a temperature in the range of about 450 to 500° F. and at pressure of about 100 to about 400 mm. Hg. The hold time in the second dehydration zone is about 1 to 2 hours to complete conversion of the trimellitic acid to its anhydride.

Liquid is withdrawn continuously from the second dehydration boiler in an amount equivalent in weight to the dry solids content of the wet cake fed to the boiler. This liquid containing crude trimellitic anhydride (3 to 5% impurities) is continuously charged to an anhydride product product distillation tower operated at a temperature in a range of about 425° F. to about 575° F. and pressure in a range of about 4 to about 100 mm. Hg absolute pressure. The vapor mixture from either product flasher passes through a hot condenser to condense only the anhydride. The liquid anhydride is cooled to a temperature in the range of about 350° F. to about 370° F. at 10 mm. Hg absolute pressure. The materials boiling below trimellitic acid are drawn off as vapors.

The liquid trimellitic anhydride condensate at about 350° F. to about 370° F. and 10 mm. Hg absolute pressure is pumped to a flaker cooled by 135° F. water. This distilled product has an anhydride purity of 97 to 99% and is recovered in a yield in the range of 89 to 91% based on the total trimellitic acid in the oxidation reaction effluent.

The combined acetic acid mother liquor, vent vapor from the first acid product dehydrator and other aqueous acetic acid liquors collected in the surge drum following filtration to recover trimellitic acid crystals is continuously charged to a stripping zone operated at 0 to 10 psig and a temperature in a range of about 220° F. to about 270° F. where substantially all of the water and acetic acid are vaporized and sent as vapor or condensate feed to a fractionation zone to concentrate to acetic acid of 94 to 98% by weight. The residue in the stripper bottoms is liquid. This liquid is heated to a temperature in a range of about 430° to 470° F. in the stripper stillpot operated at about 10–25 psia. The stripper stillpot bottoms contains 30 to 60% trimellitic anhydride. In a process of this invention up to about 50% of this residue is charged to the first product dehydration zone.

This type of oxidation reaction effluent, the dehydration-drying of acetic acid wet trimellitic acid in two zones, stripping of combined acetic acid mother liquor and first dehydration vent vapor to obtain stripper residue, the recycle of residue from the stripper stillpot to the first dehydration zone, purification by distillation of crude liquid trimellitic anhydride from the dehydration-drying liquid, and recycle of anhydride distillation bottoms to the stripper stillpot all cooperate with the preceding and following steps to provide ultimately the recovery of about 90% of the total trimellitic acid first produced as product of 97 to 99% anhydride content. The combination of those steps are essential for that result.

The following illustrative examples will demonstrate operation of the total process of this invention under preferred conditions.

EXAMPLE I

A $C_9$ aromatic hydrocarbon feed stock containing 98 weight percent pseudocumene is oxidized with air in an oxidation zone under liquid phase conditions at 320° to 410° F. and 140 to 370 psig in the presence of 2.0 weight parts of acetic acid (6% water content) solvent per weight part of $C_9$ feed stock and 0.28 weight percent total of zirconium, cobalt and manganese (calculated as metals but added as their acetates or acetate tetrahydrates) and a bromine source to provide 0.31 weight percent bromide ion. Both catalyst component concentrations are based on acetic acid solvent. The oxidation is conducted for a $C_9$ aromatic feed stock hold time of 60 minutes. This oxidation produces 157.5 pounds trimellitic acid per 100 pounds of the $C_9$ aromatic feed stock.

The oxidation reaction effluent has as solvent an aqueous acetic acid of 25% water and 75% acetic acid by weight. The oxidation reaction effluent composition is about 16% water, 43% acetic acid, 38% trimellitic acid, and 3% oxidation aromatic co-products, by-products and catalyst components. This oxidation reaction effluent is treated in the following manner where all "percents" are by weight.

The oxidation reaction effluent at about 410° F. and about 370 psig is discharged into a reactor surge vessel. The oxidation reaction effluent is cooled to about 350° F. as sensible heat is removed from the oxidation effluent by surface evaporation of acetic acid and water at a pressure of about 108 psig. Wet acetic acid vapors are condensed and sent to acetic acid concentration. The resulting liquid mass is charged to the batch crystallization vessel in which the liquid mass is cooled to about 120° F. by reducing the pressure to about 67 mm. Hg absolute pressure. Under these conditions trimellitic acid is precipitated as crystals. Again the vapors of acetic acid and water evaporated from the liquid surface are condensed and sent to acetic acid concentration.

Slurry is transferred to a rotary vacuum filter where trimellitic acid is recovered as wet filter cake. The acetic acid mother liquor is sent to acetic acid concentration for further processing to recover trimellitic acid values.

The wet cake of crystalline trimellitic acid discharged from the centrifuge contains about 66% trimellitic acid, 30% solvent and 4% impurities, mainly aromatic impurities. The wet cake is fed by screw conveyor into a first acid product dehydrator containing molten trimellitic anhydride at 445° F. and a pressure of about one atmospheric pressure. The acetic acid in the cake evaporates and the vapors, containing steam and some vaporized trimellitic anhydride, flow to acetic acid concentration. These wet acetic acid vapors are transferred as part of the feed for acetic acid concentration.

Liquid at 445° F. flows from the first to the second acid product dehydrator operated at 467° F. and pressure of about 150 mm. Hg.

Liquid at 467° F. containing trimellitic anhydride flows to the anhydride distillation tower partial vaporizer, which heats the stream to about 500° F. at a pressure of about 10 mm. Hg absolute pressure. Liquid from the bottom of the anhydride distillation tower flows to an evaporator from which vapors are returned to the bottom of the tower and a liquid bottom fraction having catalyst metals is transferred continuously to the stripper stillpot. Trimellitic anhydride vapors are taken overhead and condensed as liquid. This is about 98% of the anhydride charged to the anhydride distillation tower and is equivalent to 90% of the total trimellitic acid formed during oxidation. The purified trimellitic anhydride product has a trimellitic anhydride content of about 97.5%. The triethylene glycol color of purified trimellitic anhydride in this example measured 67.

A continuous flow of combined vapor from the first acid product dehydrator and acetic acid mother liquor obtained during filtration are charged to a stripping column, operated at a pressure of about 6 psig. A large portion of acetic acid and water vaporizes as the liquid in the column is by heated by a stripper reboiler operated at 260° F. Trimellitic acid, oxidation co-products and by-products, trimellitic anhydride, and unvaporized acetic acid flow downward through the column into the stripper stillpot. Acetic acid vaporizes and trimellitic acid dehydrates in the stripper stillpot operating at a temperature in a range of about 430° to about 470° F. and a pressure in a range of about 10 to 25 psia. The stillpot vapors pass upwardly and are returned to the stripping column. In this example stripper column residue and anhydride distillation bottoms having high melting solids and catalyst metals is continuously added to the first dehydrator at a rate of 25 weight percent of the combined residue and bottom fraction from anhydride distillation. Reflux of acetic acid solvent is added at at the top of the column. The vapors from the top of the column are removed and transferred as feed to a dehydration tower for acetic acid concentration and recycle.

EXAMPLE II

The process of Example I is repeated except the residue from the stripper stillpot is continuously added to the the first dehydrator at a rate of 50 weight percent of the combined residue and bottom fraction from anhydride distillation.

The yield of purified trimellitic anhydride product increases to an amount equivalent to 91.5% of the total trimellitic acid formed during oxidation. Triethylene glycol color of the product measured about 105 which is also an increase, but well below a typical product specification of 170 maximum.

COMPARATIVE EXAMPLE A

The process of Example I is repeated except the residue from the stripper stillpot flows to waste disposal and is not added to the the first dehydrator. Wet vapor from the first dehydration is transferred to the stripper. The bottom fraction from anhydride product distillation, having catalyst metals flows to waste disposal through the stripper stillpot.

The yield of purified trimellitic anhydride product decreases to an amount equivalent to about 88.5% of the total trimellitic acid formed during oxidation. Triethylene glycol color of the product measured about 60 which is equivalent to the TEG color of product of Example I.

BRIEF DESCRIPTION OF THE DRAWINGS

In the accompanying drawings forming part of the specification, in which like numerals are employed to designate like parts throughout the same.

DESCRIPTION OF PREFERRED EMBODIMENTS

While this invention is susceptible of embodiment in many different forms, this specification and accompanying drawings disclose only some specific forms as an example of the use of the invention. The invention is not intended to be limited to the embodiments so described, and the scope of the invention will be pointed out in the appended claims.

The apparatus of this invention is used with certain conventional components the details of which, although not fully illustrated or described, will be apparent to those having skill in the art and an understanding of the necessary functions of such components.

Figure 1:
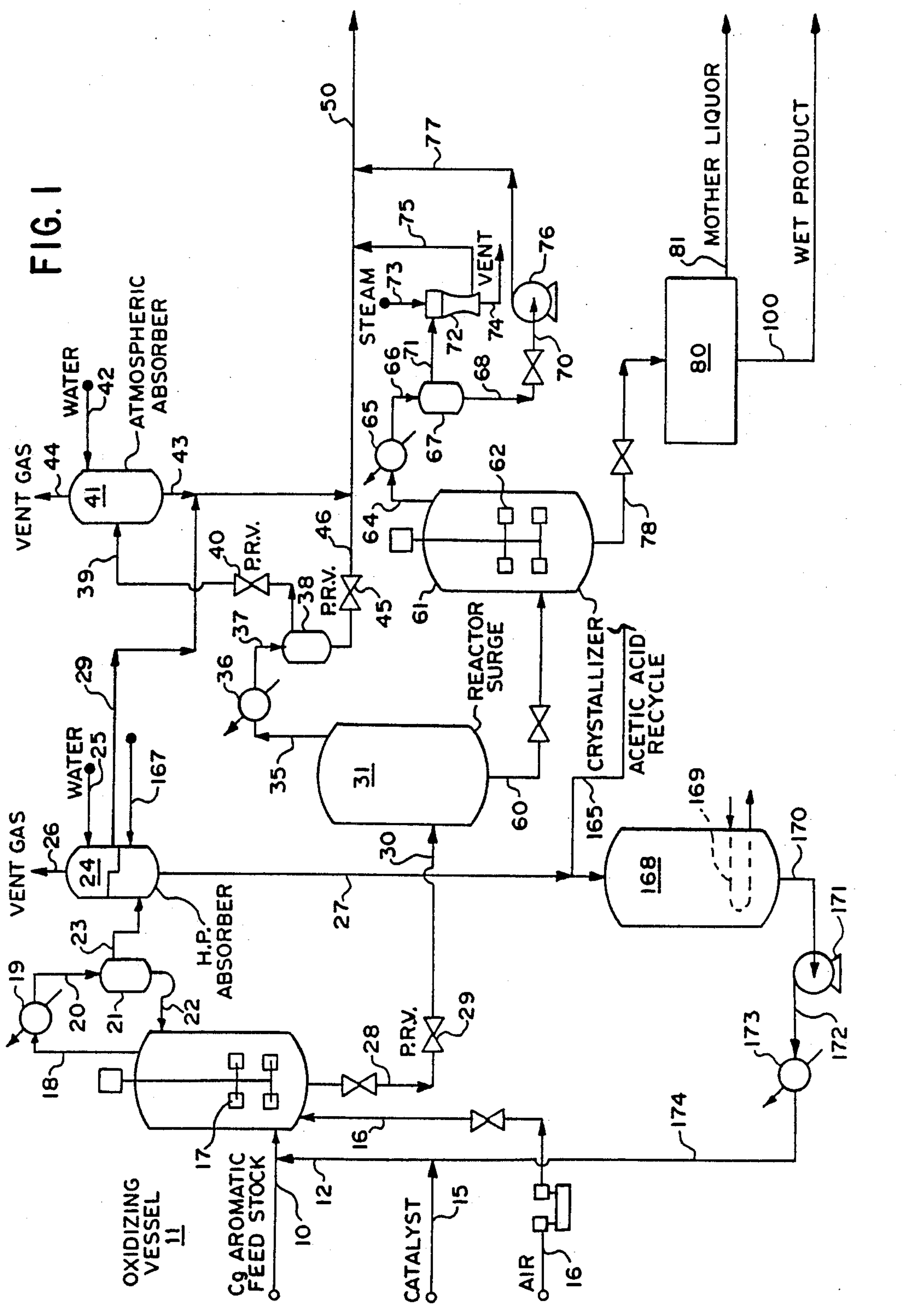
FIG. 1 is a simplified diagrammatic representation of a portion of an integrated commercial system for the manufacture of trimellitic acid and includes provisions for oxidation, introducing the materials essential for oxidation such as the trialkylbenzene feed stock, solvent, catalyst and air into the oxidation vessel, for receiving and crystallizing trimellitic acid from the effluent from the oxidation vessel and for recovering the crystallized trimellitic acid from the mother liquor.

More specifically with reference to FIG. 1, the integrated system comprises one or more oxidizing vessel, such as oxidizing vessel 11 shown with means for agitating the liquid in the oxidation zone such as stirrer 17 if desired or needed by the particular design of oxidizing vessel 11 and the manner in which gas containing free oxygen such as air is introduced into the oxidation zone. To oxidize the three methyl groups to COOH groups the theoretical oxygen is 4.5 moles per mole of pseudocumene.

The operation of the system is started by charging to oxidizing vessel 11, the $C_9$ aromatic hydrocarbon through feed stock conduit 10, solvent and catalyst through conduit 15 generally as a solution of a source of bromine such as an organic or inorganic bromide and a source of heavy metal oxidation catalyst such as a solution of a salt of the heavy metal in a small amount of water or acetic acid solvent or dissolved in the $C_9$ aromatic feed stock. Acetic acid solvent recycle is withdrawn from vessel 168 through transfer line 170 by pump 171 discharging through conduit 172 into heater 173 and transfer line 174. The acid may also be heated by coil 169 in vessel 168. As shown in FIG. 1 the ingredients that go to make up the liquid phase reaction mixture in the oxidation zone all flow into acetic acid recyle conduit 12 and thence into oxidizing vessel 11. The liquid mixture can be passed through a preheater (not shown) before entering oxidizing vessel 11 and be heated to a temperature at which oxidation will at least be initiated or the liquid mixture can be heated to reaction temperature in oxidizing vessel by the means provided for adding external heat during the latter portion of the oxidation reaction.

Pressurized air is charged through conduit 16 into the liquid phase reaction mixture through the bottom of oxidizing vessel 11. Oxidation reaction effluent is withdrawn through valved conduit 28, is discharged into reactor surge 31 through pressure reducer 29 and conduit 30 below the liquid level in reactor surge 31.

Heat is given off during the oxidation causing boil-up of solvent and/or hydrocarbon. Their vapors together with by-product water vapor leave the oxidation zone in admixture with nitrogen, unreacted oxygen and oxides of carbon. This gasiform mixture leaves oxidizing vessel 11 through conduct 18, passes through cooler 19 and conduit 20 to liquid-gas separator 21. Condensate in separator 21 is returned to oxidizing vessel 11 through conduit 22. The uncondensed gases and vapors are scrubbed in high pressure (H.P.) absorber 24 with acetic acid to remove hydrocarbons, such as pseudocumene, which are recycled to feed mix preparation through transfer line 27 where it is combined with recycle acetic acid in vessel 168. The uncondensed gases and vapors are then scrubbed with water in high pressure absorber 24 to remove acetic acid vapors and the scrubbed gases are vented by conduit 26 through a pressure control valve (not shown) to the atmosphere. The aqueous acetic acid from H.P. absorber 24 is sent to acetic acid concentration by conduits 29 and 50.

Upon completion of the oxidation reaction, liquid effluent from the oxidation zone is discharged through valved conduit 28, pressure reducer 29 and conduit 30. Reactor surge 31 can handle oxidation reaction effluent from one or more oxidizing vessels. Advantage can be taken of the pressure of and the temperature of the liquid effluent to cool the oxidation reaction effluent by removal of sensible heat as before mentioned. This can be advantageously done by flashing solvent and water in reactor surge tank 31. The resulting vapors exit through conduit 35 and are condensed by cooler 36. The condensate flows through line 37 to liquid-vapor separator 38 and the liquid is withdrawn by valved conduit 45-46 and sent via conduit 50 to acetic acid concentration. Any uncondensed gases and vapors are vented as is required through conduit 39, pressure reducing valve 40 and line 39 into atmospheric absorber 41. The aqueous acetic acid from the atmospheric absorber 41 is sent to acetic acid concentration by conduits 43 and 50. Scrubbed vapors are vented through line 44.

The amount of solvent, wet acetic acid, flashed off in surge tank 31 will depend on the temperature and pressure of the liquid effluent removed from oxidizing vessel 11.

The cooled and depressurized mixture in reactor surge 31 flows therefrom through valved conduit 60 to batch crystallizer 61 operated at reduced pressure, as before disclosed, imposed therein by any means; e.g., vacuum jet 72 through conduit 71 connected to the vapor space in liquid-gas separator 67 which receives condensate and vapors from crystallizer 61 through conduit 64, cooler 65 and conduit 66. Condensate from separator 67 can be withdrawn by pump 76, conduit 68 and valved conduit 70 for solvent concentration. Crystallizer 61 has a stirrer or agitator 62 to keep in suspension the crystallized trimellitic acid.

Separation of the solid phase (crystallized trimellitic acid) from the liquid phase (acetic acid mother liquor) can be accomplished by the use of any device for accomplishing such a phase separation. For example, the phase separation can be carried out by decantation, filtration or centrifugation. Centrifugal filters, filter presses or vacuum rotary filters can be employed for recovering the crystallized trimellitic acid from the mother liquor. The slurry of trimellitic acid crystals is withdrawn from crystallizer 61 through conduit 78 discharging into solid-liquid separator 80 to obtain a trimellitic acid crystal cake. Mother liquor is collected through conduit 81 in mother liquor surge 82 shown on FIG. 2. Wet cake is discharged through transfer line 100 to acid product dehydrator 200 shown in FIG. 3. Transfer line 100 is preferably a screw conveyor although belt or scoop conveyors can also be used in this service.

Figure 2:
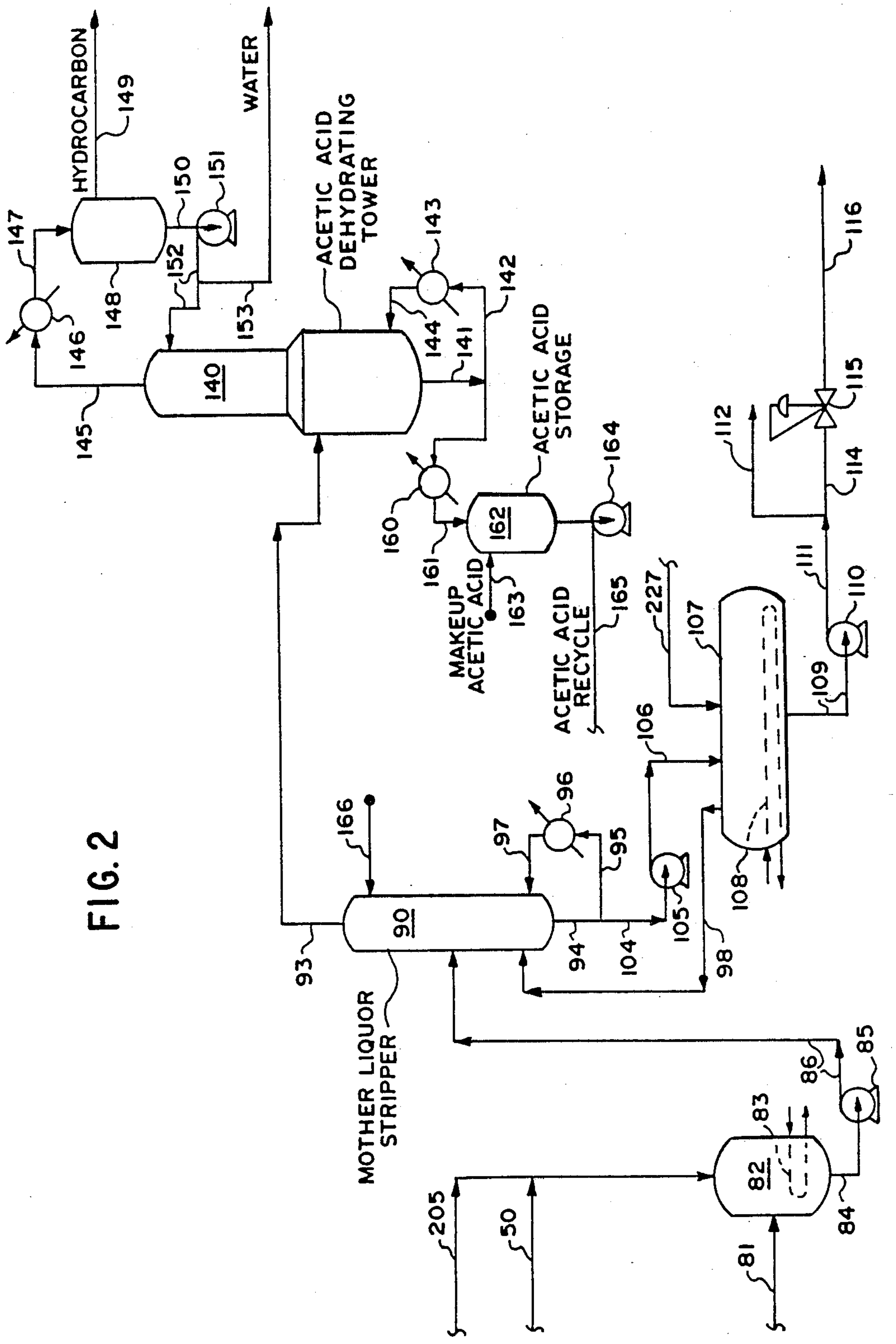
FIG. 2 illustrates diagrammatically a system for processing the mother liquor and other solvent containing streams with provisions for stripping wet acetic acid from the mother liquor, concentrating wet acetic acid, recycling concentrated acetic acid and for processing aromatic compounds dissolved in the mother liquor.

FIG. 2 illustrates the portion of the integrated system for processing acetic acid. Here the mother liquor from recovery of solid trimellitic acid collected in mother liquor surge 82 is charged through conduit 84 by pump 85 and conduit 86 into mother liquor stripper 90. The stripper feed contains trimellitic acid and aromatic co-products and by-products as before described. A mixture of water and acetic acid vapors is removed from the top of mother liquor stripper 90 by vapor transfer conduit 93 and charged directly into acetic acid dehydration tower 140. Water vapor with a small amount of acetic acid vapor and any pseudocumene present comes off as overhead through vapor line 145 through cooler 146 and condensate line 147 to separator 148 where hydrocarbon is drawn off via line 149 when need be. A part of the water condensate is returned as reflux as shown. Acetic acid of 93 to 98% by weight is withdrawn from the bottom of acetic acid dehydrating tower 140 through conduit 141, cooled by heat exchanger 160 and collected in acetic acid storage tank 162. Makeup acetic acid is charged to tank 162 through line 163. Acetic acid for charging oxidizing vessel 11 is withdrawn by pump 164 discharging into conduit 165. Recycle acetic acid is used as reflux for the mother liquor stripper. Liquid from the bottom of stripper 90 flows through transfer lines 94 and 95 to boiler 96. Liquid-gas effluent from boiler 96 is charged to the bottom of stripper 90. The stripper bottoms liquid is withdrawn through transfer line 104 by pump 105 discharging though line 106 into stripper stillpot vessel 107 heated, for example by coil 108. Vapor from the stripper stillpot 107 flows into stripper 90 through vapor transfer line 98.

Figure 3:
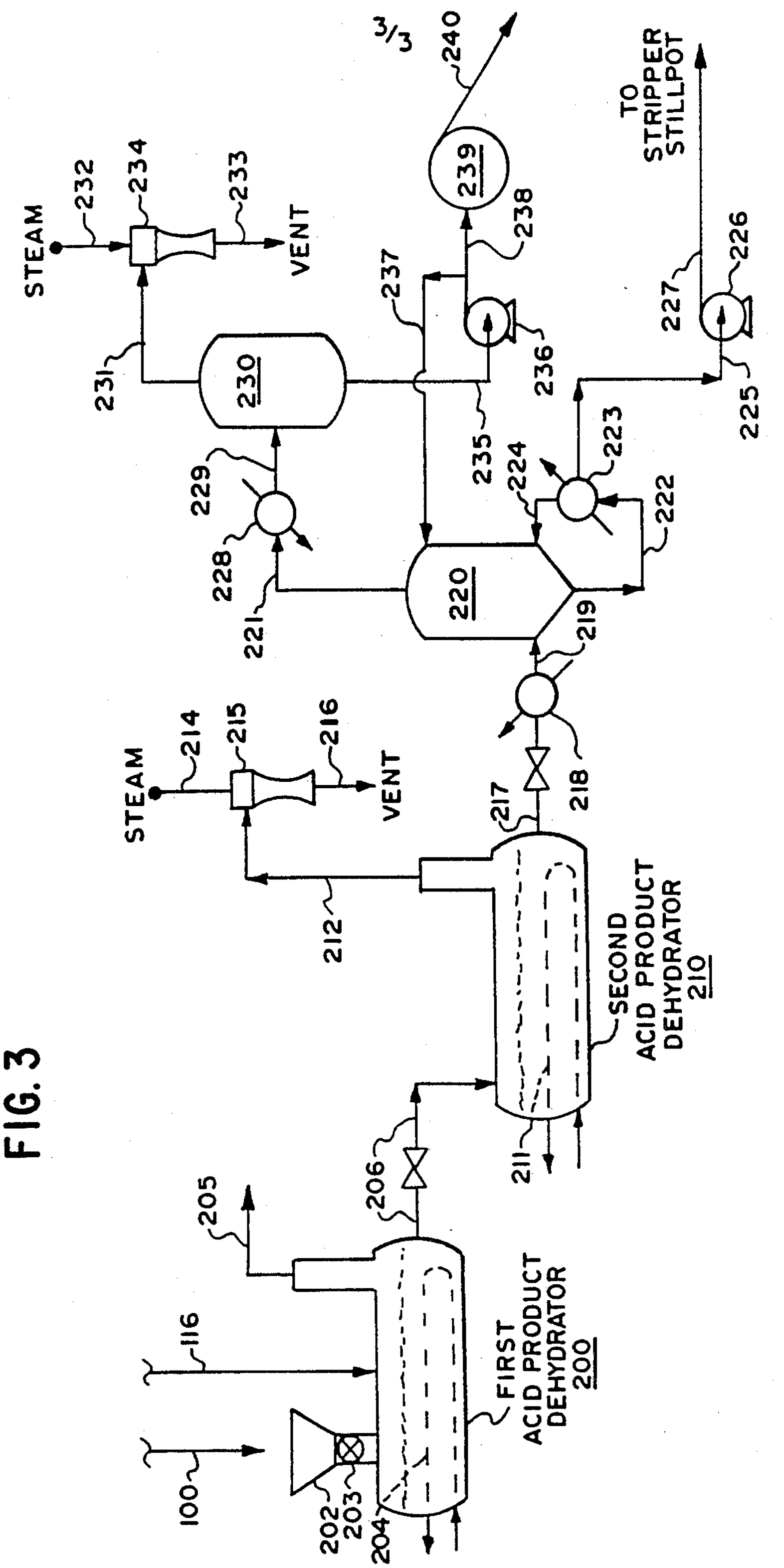
FIG. 3 illustrates diagrammatically a system for converting trimellitic acid to its anhydride including two dehydration vessels, a means for separating a purified anhydride product from impurities concentrated in the crude anhydride product and a means for preparing the anhydride in a form ready for shipment and/or use as a starting material for use in chemical reactions.

A bottom fraction from distillation of crude trimellitic anhydride product, shown on FIG. 3, flows into the stripper stillpot 107 through conduit 227 and the bottom fraction is admixed with the liquid in the stripper stillpot 107 forming a residue having high melting solids and catalyst metals. The residue is withdrawn from the stripper stillpot 107 through transfer line 109 (heat traced) by pump 110 discharging through heat traced line 111. A fraction of the residue flows to waste disposal through conduit 112 and a fraction of the residue flows to the first acid product dehydrator 200, shown on FIG. 3, through conduit 114, flow controller 115 and transfer line 116.

Now turning to FIG. 3, the wet cake from solid-liquid separator 80 is fed through transfer line 100 to hopper 202 and thence by screw feed 203 into first acid product dehydrator 200 that contains a molten crude anhydride. The wet cake charged to the molten liquid in acid product dehydrator 200 heated as by means of internal coil 204 or other heat exchanger in which, for a source of heat, can be any fluid remaining liquid, the temperature employed to dehydrate trimellitic acid to its anhydride. Advantageously, liquids are fed to internal coil 204 at about 600° to 700° F. Such materials as diphenyl oxide, chlorinated biphenyls, and chlorinated terphenyls which are fluids at 400° to 700° F. can be employed as heat transfer media. As the wet cake is introduced into dehydrator 200, the adhering acetic acid and water of dehydration flash off and are withdrawn as vapors through conduit 205 to mother liquor surge vessel 82. Residue from the stripper stillpot is added to the first dehydrator 200 through line 116.

The thermal dehydration of trimellitic acid to its anhydride in the first acid product dehydrator 200 is conducted at about atmospheric pressure. Effluent from the first acid product dehydration 200 flows into the second acid product dehydration 210 through valved transfer line 206. The second dehydrator 210 operates at a pressure below atmospheric, preferably at a pressure less than about 550 mm. Hg absolute, which pressure is maintained by vacuum jet 215. The pool of liquid is heated by coil 211 or an external heat exchanger, similar to the first dehydrator 200.

After dehydration, the crude trimellitic anhydride product is processed to obtain a product having a high anhydride content, 97% or above by withdrawing a portion of the liquid from acid product dehydrator 210 through valved conduit 217 to anhydride distillation 220 supplied by heat for example by vaporizer 218. Trimellitic acid anhydride is distilled using as reflux liquid trimellitic anhydride product through conduit 237. The anhydride vapors are transferred by conduit 221 through vapor cooler 228 and conduit 229 that discharges into liquid anhydride product receiver 230. Light ends are removed from liquid anhydride product receiver 230 through conduit 231 by steam jet 234.

Liquid anhydride product is withdrawn from liquid anhydride product receiver 230 through transfer line 235 by pump 236 and discharged through transfer line 238 into flaker 239 where the liquid anhydride product is finally cooled and flaked. The flaked product is discharged down chute 240 to storage or packaging.

The bottoms from the anhydride distillation tower flow through conduit 222 to evaporator 223, for example a Kontro thin film evaporator, Trimellitic anhydride vapors return to tower 220 through conduit 224. Concentrated bottoms containing catalyst metals and high boiling compounds are transferred to the stripper still-pot 107 through conduits 225 and 227 by pump 226.

We claim:

1. An improved process for the manufacture of trimellitic acid anhydride having a 97 to 98% anhydride content and having a triethylene glycol color of 170 or less, in yields in the range of 89 to 90% and higher based on the total trimellitic acid produced by catalytic air oxidation of pseudocumene, including the steps of catalytic oxidation of pseudocumene in the presence of acetic acid in an oxidation zone wherein liquid-phase conditions are maintained and wherein the weight ratio of acetic acid to pseudocumene is in the range of about 0.5–5.0:1.0 and the catalyst comprises one or more heavy metal oxidation catalysts comprising zirconium, cobalt, and manganese to provide about 0.1 to about 0.4 weight percent total metals based on pseudocumene and a source of bromine and to provide a total of about 0.1 to about 0.3 weight percent total bromine based on pseudocumene, wherein the total weight ratio of bromine ions to total metal ions is about 0.5 to about 2.0, the zirconium content is about 1 to about 5%, and the manganese content is about 14 to about 60%, each metal by weight of the total metals and wherein the cobalt content is about 35 to about 80 weight percent, temperatures in the oxidation are in a range of about 220° F. to about 480° F., cooling the oxidation reaction effluent to crystallize trimellitic acid, separating and recovering crystallized trimellitic acid from the acetic acid solvent mother liquor, distilling from the acetic acid mother liquor to obtain a mixture of acetic acid and water for concentration of the acetic acid content to provide acetic acid solvent concentrate for recycle to the oxidation and to obtain a bottoms fraction containing high melting solids, heating the crystalline trimellitic acid to convert it to its anhydride and distilling the anhydride to obtain trimellitic acid anhydride product; the improvements comprising conducting the conversion continuously in two series staged dehydration zones with heat removal by evaporation from the liquid in each of the dehydration zones operated at temperatures in a range of about 400° to about 500° F. thereby converting trimellitic acid to its anhydride and evaporating acetic acid solvent, distilling the liquid crude trimellitic anhydride, condensing the vaporized overhead fraction to obtain trimellitic anhydride product, combining the vapor from the first dehydration zone and the acetic acid mother liquor as feed for distilling acetic acid and water mixture therefrom leaving the residue containing high melting solids, combining the residue and the bottom fraction from the distillation of the trimellitic anhydride containing catalyst metals, and continuously adding up to about 50 weight percent of the combined residue and bottom fraction containing high melting solids and catalyst metals to the first dehydration zone.

2. The process of claim 1 wherein the first dehydration zone is operated at temperatures in a range of about 420° to about 480° F. and at a pressure in a range of about 10 to about 25 pounds per square inch absolute and the second dehydration zone is operated at a temperature in a range of about 420° to about 490° F. and a pressure in the range of about 50 to about 400 mm. Hg thereby converting trimellitic acid to its anhydride.

3. The process of claim 2 wherein the crude trimellitic anhydride is distilled at a temperature in a range of about 425° to about 575° F. and an absolute pressure in a range of about 4 to about 400 mm. Hg absolute.

4. The process of claim 3 wherein the weight percent of the combined residue and bottom fraction continuously added to the first dehydration zone is controlled to an amount in a range of from about 10 to about 45 weight percent of the combined residue and bottom fraction.

5. The process of claim 1 wherein the first dehydration zone is operated at temperatures in a range of about 420° to about 480° F. and at a pressure in a range of about 10 to about 25 pounds per square inch absolute and the second dehydration zone is operated at a temperature in a range of about 420 to about 490 F. and a pressure in the range of about 50 to about 400 mm. Hg thereby converting trimellitic acid to its anhydride, the crude trimellitic anhydride is distilled at a temperature in a range of about 450° to about 550° F. and an absolute pressure in a range of about 4 to about 300 mm. Hg absolute, and the weight percent of the combined residue and bottom fraction continuously added to the first dehydration zone is controlled to an amount in a range of from about 20 to about 35 weight percent of the combined residue and bottom fraction.

* * * * *